(12) United States Patent
Matsumoto et al.

(10) Patent No.: US 7,382,462 B2
(45) Date of Patent: Jun. 3, 2008

(54) DEVICE FOR MEASURING THE REFLECTION FACTOR

(75) Inventors: Shigeki Matsumoto, Himeji (JP);
Shigenori Nozawa, Himeji (JP);
Yoshimasa Ogawa, Himeji (JP)

(73) Assignee: Ushiodenki Kabushiki Kaisha, Tokyo (JP)

( * ) Notice: Subject to any disclaimer, the term of this patent is extended or adjusted under 35 U.S.C. 154(b) by 332 days.

(21) Appl. No.: 11/355,106

(22) Filed: Feb. 16, 2006

(65) Prior Publication Data

US 2006/0186407 A1 Aug. 24, 2006

(30) Foreign Application Priority Data

Feb. 23, 2005 (JP) .............................. 2005/046560

(51) Int. Cl.
*G01N 21/55* (2006.01)
*G01N 21/47* (2006.01)

(52) U.S. Cl. ....................... 356/445; 356/446
(58) Field of Classification Search ..................... None
See application file for complete search history.

(56) References Cited

U.S. PATENT DOCUMENTS 4,632,559 A 12/1986 Brunsting

FOREIGN PATENT DOCUMENTS

| DE | 89 07 969.8 U1 | 9/1989 |
|---|---|---|
| EP | 0 182 647 A2 | 5/1986 |
| EP | 1 484 601 A2 | 12/2004 |
| GB | 1 522 965 | 8/1978 |
| JP | 2001-141644 | 5/2001 |
| WO | 99/35487 A1 | 7/1999 |

OTHER PUBLICATIONS

European Search Report Dated Dec. 27, 2007 Re Application No. EP 06 00 3080.

*Primary Examiner*—Gregory J. Toatley, Jr.
*Assistant Examiner*—Amanda H Merlino
(74) *Attorney, Agent, or Firm*—David S. Safran

(57) ABSTRACT

A device for measuring the reflection factor by irradiating a measurement area of a microchip with light, and in which a light receiving part is made to receive light reflected from the measurement area for determination of the reflection factor of the measurement area. The light receiving part is located in an angular region $\theta$, satisfying the relationship $(\frac{1}{2})\alpha \leq \theta \leq \sin^{-1}(1/n)$ and being located between angles $\theta_{min}$ and $\theta_{max}$, $\theta_{min}$ and $\theta_{max}$ (in°) being angles which the reflection light forms with respect to a normal on the edge of the irradiated surface of the area to be measured in a virtual plane which contains the emission center of the light emitting part and which is perpendicular to the microchip, wherein $\theta_{min}$ is $\frac{1}{2} \alpha$ and $\theta_{max}$ corresponds to $\sin^{-1}(1/n)$, where $\alpha$ (°) is the scattering angle of the light radiated by the light emitting part which is located directly above the area to be measured, and wherein n is the index of refraction of the transparent component.

4 Claims, 4 Drawing Sheets

| Sample | | Absorption wavelength (nm) of sample after reaction with reagent |
|---|---|---|
| Liver function | γ-GTP | 405 |
| | GOT | 340 |
| | GPT | 340 |
| | ALP | 415 |
| Kidney function | BUN | 340 |
| | Cre | 600 |
| | UA | 600 |
| Blood sugar value | GA | 550 |

| → | Light reflected from the surface of the transparent part | ▬ | Reaction substrate |
| ----- | ----- | ----- | ----- |
| ---→ | Light reflected and scattered from the reaction substrate | ------- | Direction property of PD (detector) |

→ Light reflected from the surface of the transparent part

--→ Light reflected and scattered from the reaction substrate

▬ Reaction substrate

------ Direction property of PD (detector)

DEVICE FOR MEASURING THE REFLECTION FACTOR

BACKGROUND OF THE INVENTION

1. Field of the Invention

The invention relates to a device for measuring the reflection factor. The invention relates especially to a device for measuring the reflection factor for blood analyses and chemical analyses in which the concentrations of given components in samples are determined by the reflection factors of light with certain wavelengths.

2. Description of Related Art

Conventionally, a process in which the reflection factor at a certain wavelength is measured is known as a process for measuring the concentration of a component in a sample based on the color of a reaction substrate, for example, a reaction paper.

As FIG. 8 shows, Japanese Patent Application JP-A-2001-141644 discloses a device for measuring the reflection factor in which a reaction substrate is irradiated obliquely from overhead with light of a certain wavelength and in which the reflected light is determined directly above the reaction substrate. In this device for measuring the reflection factor, the use of a relatively large amount of the sample liquid (ml amount) is possible, and to a certain degree, the measurement is not adversely affected in the reaction substrate itself when the sample liquid volatilizes.

In the case of using blood or the like as the sample, a device is wanted in which a measurement is possible for an extremely small amount of sample (µl amount). However, in the device shown in FIG. 8 for measuring the reflection factor in the prior art, there is the disadvantage that at an extremely small amount of the sample volatilizes. Especially when using the above described sample, there are many cases of the use of enzyme reactions. In these cases, the sample itself is heated, by which more sample is vaporized.

To prevent vaporization, it can be envisioned that the reaction substrate might be coated with a transparent component. In the above described process in which the reflection light is received by the conventional oblique light irradiation directly above the reaction substrate, there are, however, the disadvantages that the light which has been reflected by the transparent substrate leads to faulty radiation which is captured by the detector and that the sensitivity of determination decreases.

SUMMARY OF THE INVENTION

The present invention was devised to eliminate the above described disadvantage in the prior art. Thus, a primary object of the this invention is to devise a device for measuring the reflection factor in which, even if an area to be measured on a microchip (a reaction substrate such as, for example, reaction paper) has been coated with a transparent component and the amount of the sample in the area to be measured is extremely small, that is, in the microliter range, advantageous sensitivity of determination can be obtained.

This object is achieved by the invention as follows:

In a first aspect of the invention, in a device for measuring the reflection factor which has a light emitting part from which light with a certain wavelength and directional capacity emerges, and a light receiving part, in which, furthermore, the area of the microchip which is to be measured is irradiated with light from the light emitting part, in which the light reflected by the area to be measured is received by the light receiving part, and in which the reflection factor of the area to be measured is measured, this object is achieved in that the area of the microchip to be measured is covered with a transparent component, that the light emitting part is located directly above the area to be measured, that the surface irradiated by the light emitting part lies within the area to be measured and that the light receiving part is located in an angular region θ (in °) which is located between angles $\theta_{min}$ and $\theta_{max}$, $\theta_{min}$ and $\theta_{max}$ (in °) being angles which the reflection light forms with respect to a normal on the edge of the irradiated surface of the area to be measured in a virtual plane which contains the emission center of the light emitting part and which is perpendicular to the microchip, wherein $\theta_{min}$ is 1/2 α and $\theta_{max}$ corresponds to $\sin^{-1}(1/n)$, where α (°) is the scattering angle of the light radiated by the light emitting part which is located directly above the area to be measured, and wherein n is the index of refraction of the transparent component, and in which the relationship $(1/2)\alpha \leq \theta \leq \sin^{-1}(1/n)$ is satisfied. The light emitting part being located directly above the measuring area means that the light emitting part is arranged vertically above the area to be measured and is not laterally displaced.

In a second aspect of the invention, in the device for measuring the reflection factor according to the first aspect, the object is achieved in that, in a microchip with several areas to be measured, there are several light emitting parts and a light receiving part which is common to the several light emitting parts, that the respective light emitting part is located directly above the area to be measured and the light receiving part receives the light from the respective area to be measured.

In a third aspect of the invention, in the device for measuring the reflection factor according to the first aspect, the object is achieved in that, in a microchip with several areas to be measured, there are several light emitting parts and several light receiving parts, that the light emitting parts are located directly above the respective area to be measured, that the front of the respective light receiving part is provided with a focusing lens and only the light of the respective area to be measured which corresponds to the respective light receiving part is received.

Action of the Invention

In a device for measuring the reflection factor which has a light emitting part from which light with a certain wavelength and directional capacity emerges, and a light receiving part, in which the area of the microchip to be measured is irradiated with the light from the light emitting part, in which the light reflected by the area to be measured is received by the light receiving part, and in which the reflection factor of the area to be measured is measured, the object is achieved by the invention described in the first aspect in that the area of the microchip to be measured is coated with a transparent component, that the light emitting part is located directly above the area to be measured, that the surface which has been irradiated by the light emitting part lies within the area to be measured and the light receiving part is located in an angular region θ (in °) which is located between angles $\theta_{min}$ and $\theta_{max}$, $\theta_{min}$ and $\theta_{max}$ (in °) being angles which the reflection light forms with respect to a normal on the edge of the irradiated surface of the area to be measured in a virtual plane which contains the emission center of the light emitting part and which is perpendicular to the microchip, wherein $\theta_{min}$ is 1/2 α and $\theta_{max}$ corresponds to $\sin^{-1}(1/n)$, where α (°) is the scattering angle of the light radiated by the light emitting part which is located directly above the area to be measured, and wherein n is the index of refraction of the transparent component, and in that the relationship $(1/2)\alpha \leq \theta \leq \sin^{-1}(1/n)$ is satisfied. This measure can avoid the disadvantages in the prior art, specifically, that the light reflected from the transparent component leads to faulty radiation which is captured by the detector, and the determination sensitivity decreases, and also in the case of an extremely small amount of sample in the microliter range at the point to be measured, an advantageous determination sensitivity is obtained.

The invention described in the second aspect achieves the object in that in a microchip with several areas to be measured, there are several light emitting parts and a light receiving part which is common to the several light emitting parts, that the light emitting parts are located directly above the respective area to be measured and the light receiving part receives the light of the respective area to be measured. As a result of switching over the light emitting parts per area to be measured, only a single light receiving part is needed, by which the device is simplified, and moreover, measurement becomes faster.

The invention described in the third aspect achieves the object in that, in a microchip with several areas to be measured, there are several light emitting parts and several light receiving parts, that the light emitting parts are located directly above the respective area to be measured, that the front of the respective light receiving part is provided with a focusing lens and only the light of the respective area to be measured which corresponds to the respective light receiving part is received. By this measure, the light receiving area can be limited only to the respective area to be measured, and therefore, the effect of nonuniform reflection light (faulty radiation) on the measuring chamber wall can be reduced. Furthermore, several articles can be measured at the same time.

The invention is further described below reference to the embodiments shown in the accompanying drawings.

DETAILED DESCRIPTION

Figure 1:
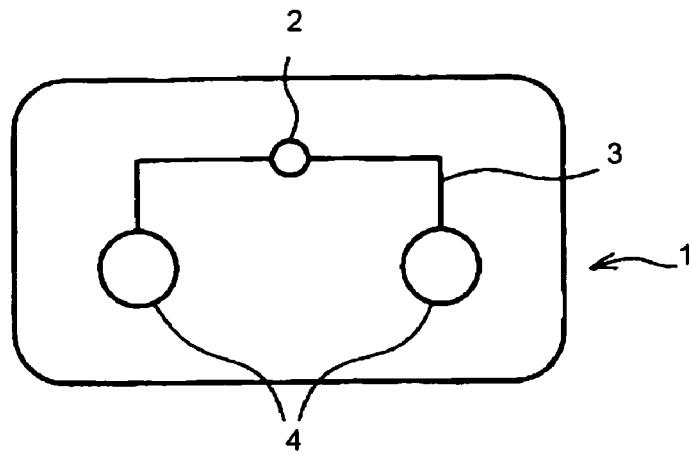
FIGS. 1(a) & 1(b) are schematic plan and side sectional views, respectively, of the arrangement of a first embodiment of a microchip which is used for the device in accordance with the invention for measuring the reflection factor.
Figure 1:
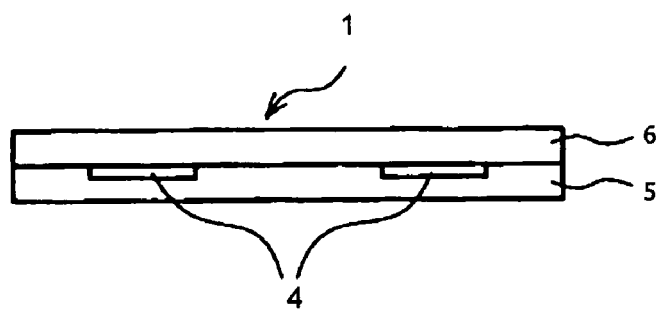

A first embodiment of the invention is described below using FIGS. 1 to 4.

FIGS. 1(a) & 1(b) schematically depict the arrangement of a microchip which is used for the device for measuring the reflection factor of the invention according to a first embodiment. The microchip 1 has an opening 2 for introducing a sample. An extremely small groove 3 on the substrate 5 is used to allow the sample which has been introduced from the opening 2 to flow to the reaction substrate 4. On the reaction substrate 4, the inflowing sample reacts with the reagent. The reaction substrate 4 constitutes the area to be measured. On the side with the opening 2, the passage 3, and the reaction substrate 4, the top of the substrate 5 is covered with a transparent component 6.

The substrate 5 is, for example, PET, PMMA, or the like. The reaction substrate 4 is, for example, formed of a porous body of nitrocellulose and contains a given reagent. The transparent component 6 is, for example, PET (index of refraction 1.6, critical angle 38.7°), (index of refraction 1.49, critical angle 42.2°), Pyrex® glass (index of refraction 1.47, critical angle 42.9°) or the like.

For example, in a blood analysis, when plasma from which the blood cells have been separated is introduced, plasma flows out of the opening 2 by the capillary action in the passage 3, and reaches the reaction substrate 4 as the area to be measured.

Figure 2:
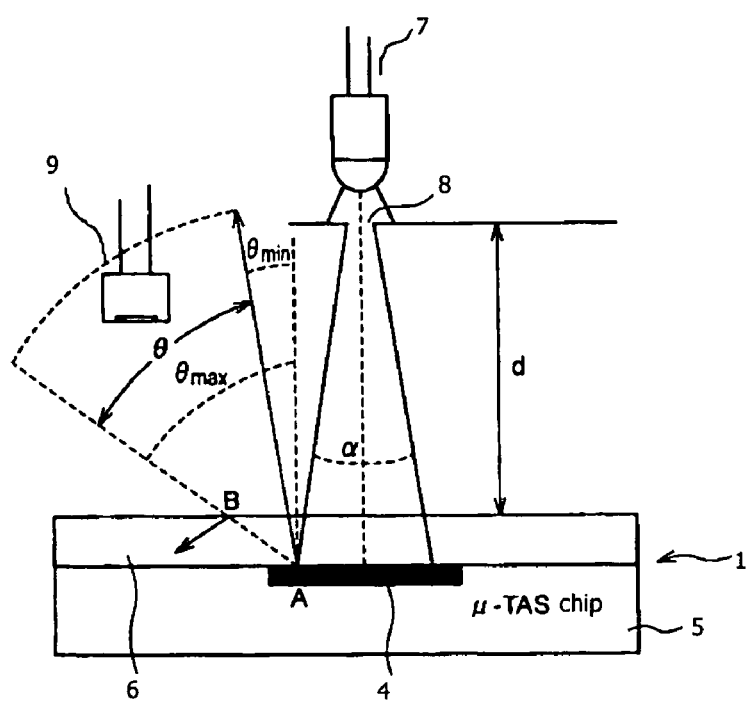
FIG. 2 is a cross section of the arrangement of the first embodiment of the device of the invention for measuring the reflection factor in a front view.

FIG. 2 is a cross section of the arrangement of this embodiment of the device for measuring the reflection factor of the invention in a front view. A universal LED 7 (light source) radiates light with certain wavelengths. An aperture 8 is arranged to prevent faulty radiation and is intended to restrict light scattering and to limit the area to be irradiated on the reaction substrate 4. A light emitting part with a certain wavelength and a directional capacity can be formed by the universal LED (light source) 7 and the aperture 8. For the light emitting part, not only does the arrangement of a universal LED (light source) and aperture 8 apply, but it can also be formed from a LED with a directional capacity, a LD (laser diode), a filament lamp, a bandpass filter, and an aperture, or also from a discharge lamp (xenon lamp or mercury lamp), a bandpass filter and an aperture. A detector 9 of a PD (photo diode) or a photomultiplier tube (PMT) corresponds to the light receiving part. The remaining arrangement corresponds to the arrangement provided with the same reference numbers in FIG. 1.

Here, the light emitting part comprises a universal LED (light source) 7 and an aperture 8 is located directly above the reaction substrate 4 as the area to be measured. The area irradiated by the light emitting part is located on the reaction substrate 4. The term "emission center point" in the invention is defined as the middle of the aperture opening in a light emitting part which is constituted by a combination of a universal LED, a filament lamp or a discharge lamp with an aperture.

The arrangement area $\theta$ of the detector 9 as the light receiving part is the area which is larger than $\theta_{min}$, where the light which has been reflected from the back (point A in the drawings) of the transparent component 6 is not incident. This area is, moreover, smaller than the critical angle $\theta_{max}$ at which the light which has been scattered by the reaction substrate 4 on the boundary (point B in the drawings) between the transparent component 6 and the air undergoes total reflection. More specifically, the detector 9 is placed in the angular region in which the relation $(1/2)\alpha \leq \theta \leq \sin^{-1}(1/n)$ is satisfied, where $\theta$ (°) is the angle which the reflection light forms with respect to a normal on the edge of the surface of the reaction substrate 4 to be irradiated on a virtual surface which contains the emission center point of the universal LED (light source) 7 and which is perpendicular to the microchip 1, where α (°) is the scattering angle of the light emitted from the light emitting part comprised of the universal LED (light source) 7 and the aperture 8, and where n is the index of refraction of the transparent component 6.

In this arrangement of the device for measuring the reflection factor,. the following measure can avoid the conventional disadvantages that the light which has been reflected from the transparent component 6 leads to faulty light which is captured by the detector 9, and the determination sensitivity drops:

The reaction substrate 4 of the microchip 1 is irradiated with light from the light emitting part of the universal LED (light source) 7 and the aperture 8;

the light reflected from the reaction substrate 4 is received by the detector 9 and the reflection factor of the reaction substrate 4 is measured.

Figures 3, 4:
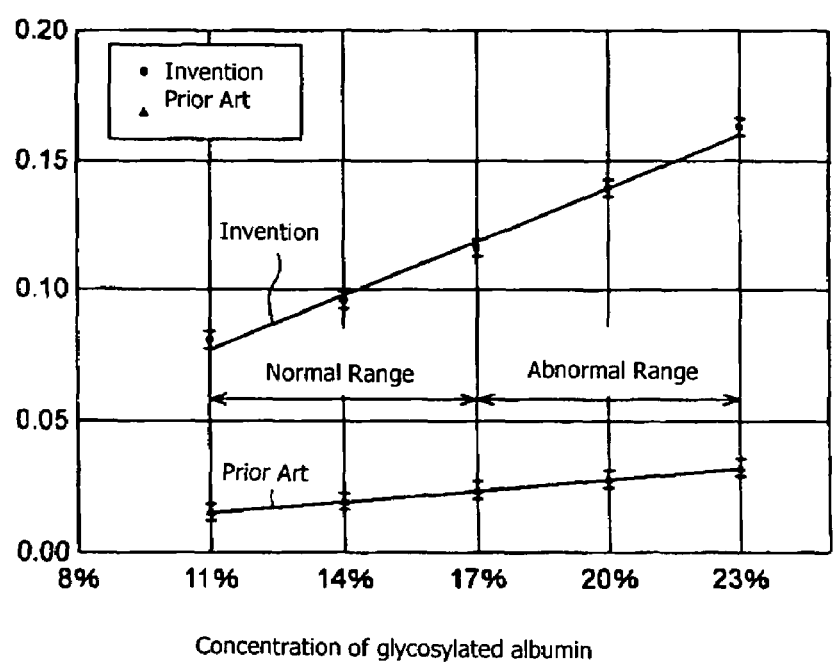
FIG. 3 shows a table of the relation between enzymes as test substrates in the blood and the absorption wavelengths of the reaction products (reactants) which have reacted with a reagent.
FIG. 4 is a graphic representation of the measurement results of a device for measuring the reflection factor according to the first embodiment and using the prior art device for measuring the reflection factor of FIG. 8.

FIG. 3 is a table showing the relation between enzymes as test substances in the blood and absorption wavelengths of the reaction products (reactants) which have reacted with reagent. The reagent differs according to the enzyme. The respective enzyme reacts with the corresponding reagent and produces a stain.

As shown in FIG. 3:

the absorption wavelength of the reaction product γ-GTP (γ-glutamyl-trans-peptidase) is 405 mm;

the absorption wavelength of the reaction product GOT (glutamate-oxalacetate-transaminase) is 340 mm;

the absorption wavelength of the reaction product GPT (glutamate-pyruvate-transaminase) is 340 mm;

the absorption wavelength of the reaction product ALP (alkali phosphatase) is 415 mm;

the absorption wavelength of the reaction product BUN (blood urea-nitrogen) is 340 mm;

the absorption wavelength of the reaction product Cre (creatine) is 600 mm;

the absorption wavelength of the reaction product UA (uric acid) is 600 mm; and the absorption wavelength of the reaction product GA (glycosylated albumin) is 550 mm.

Figure 8:
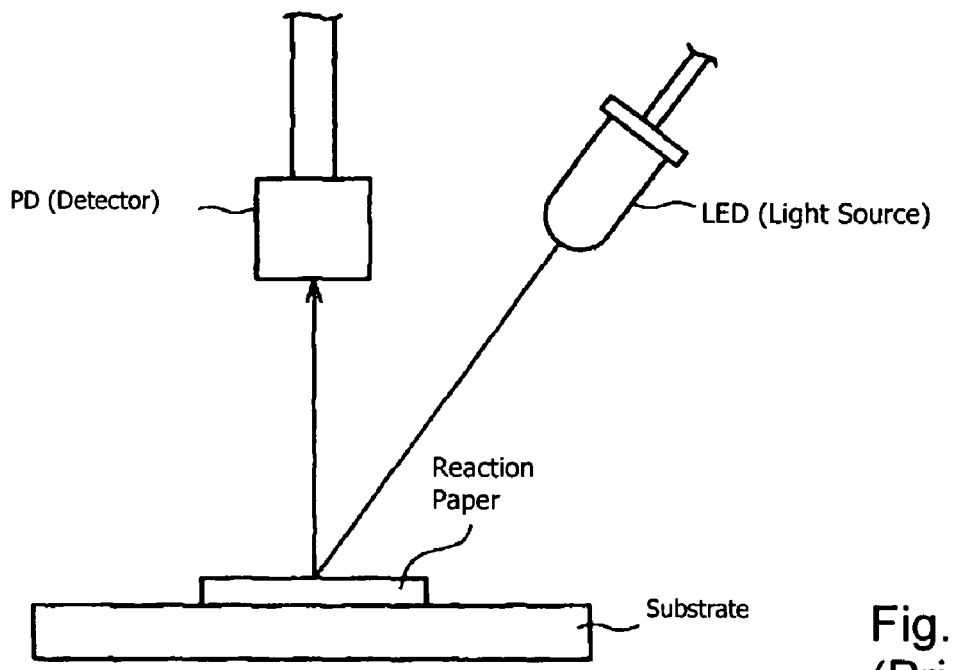
FIG. 8 schematically shows the arrangement of a prior art device for measuring the reflection factor.

FIG. 4 is a graphic representation of the results of measuring a glycosylated amino acid solution which has been prepared in a GA concentration which is known beforehand, using the device for measuring the reflection factor in accordance with the invention, according to this embodiment, and using a device for measuring the reflection factor in the prior art (FIG. 8). In the figure, the x-axis plots the GA concentration and the y-axis plots the absorbance which was computed based on $-\log_{10}$ (reflection factor).

The conditions in this measurement are described below:

distance d between the aperture and the microchip: 10.7 mm aperture diameter: Φ1 scattering angle a of the light: roughly 10°;

point(spot) diameter of the irradiation: roughly Φ3;

light source: LED (wavelength 558 nm);

material of the transparent component: PET (index of refraction 1.6);

thickness of the transparent component: 0.1 mm;

critical angle $\theta_{max}$: 38.7° and diameter of the reaction substrate: Φ4.

Since glycosylated protein and the reagent react with one another in GA, and thus, a blue-violet stain is produced, the glycosylated protein being formed by bonding of glucose and albumin in the blood, the stain was irradiated with light with a wavelength of 558 nm which is absorbed by this stain, and thus, the amount of reflection light was measured.

FIG. 4 shows that the device for measuring the reflection factor of the invention according to this embodiment has improved the slope of the calibration curve by roughly four times that of the conventional device for measuring the reflection factor, when a reaction substrate is placed on the substrate, a microchip which is coated with a transparent component is irradiated obliquely from overhead with light, and the light is received directly above the reaction substrate. By increasing the slope of the calibrating curve, normal values can be clearly distinguished from abnormal values without the error regions overlapping. In the device for measuring the reflection factor in the prior art, conversely, the normal area is roughly 11% to 17%. With an examination of the error regions, an exact diagnosis cannot be made since the abnormal values are mixed up with the normal values.

With the device for measuring the reflection factor in accordance with the invention, according to this embodiment, the light which has been reflected and scattered from the reaction substrate can be received with high efficiency, since the light which has been reflected from the surface and the back of the transparent component is not incident in the detector. Thus, the measurement resolution can be increased since the change of the reflection factor with respect to the sample concentration becomes greater.

A second embodiment of the invention is described below using FIG. 5.

Figure 5:
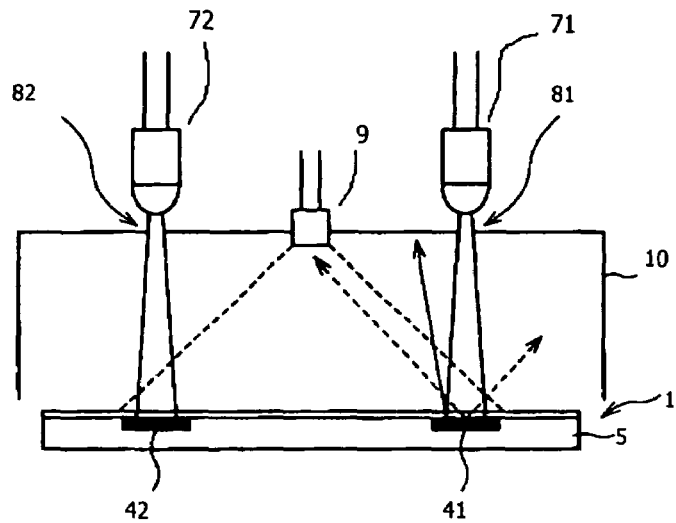
FIG. 5 is a cross section of the arrangement of a second embodiment of the device in accordance with the invention for measuring the reflection factor in a front view.

FIG. 5 shows a cross section of the arrangement of the device for measuring the reflection factor of the invention according to this embodiment in a front view. On several reaction substrates 41, 42, which constitute the areas to be measured, the inflowing sample reacts with reagent. The device comprises several universal LEDs (light sources) 71, 72, from which light with a certain wavelength emerges, and several apertures 81, 82, which are arranged like the aperture 8 shown in FIG. 2 to prevent faulty radiation and are intended to prevent light scattering and to delineate the areas to be irradiated on the reaction substrates 41, 42, and a measurement chamber 10. Other elements of the arrangement correspond to those in FIG. 2 and are labeled with the same reference numbers.

This device for measuring the reflection factor with respect to a microchip 1 with several reaction substrates 41, 42, as the areas to be measured has a detector 9 which is common to several light emitting parts which each comprise a universal LED (of a light source) 71, 72, and an aperture 81, 82. The respective light emitting part (universal LED (light source) 71+ aperture 81 and universal LED (light source) 72+ aperture 82) is placed directly above the respective reaction substrate 41, 42. The detector 9 receives the light of the respective reaction substrate 41, 42.

By this arrangement of the device for measuring the reflection factor, in addition to the action of the device for measuring the reflection factor in accordance with the invention according to the first embodiment, by switching over the light emitting parts which are in operation (universal LED (light sources) 71, 72 and apertures 81, 82) per reaction substrate 41, 42 a simplification of the device and an increase in the rate of measurement can be achieved, and only a single detector 9 is needed.

Figure 6:
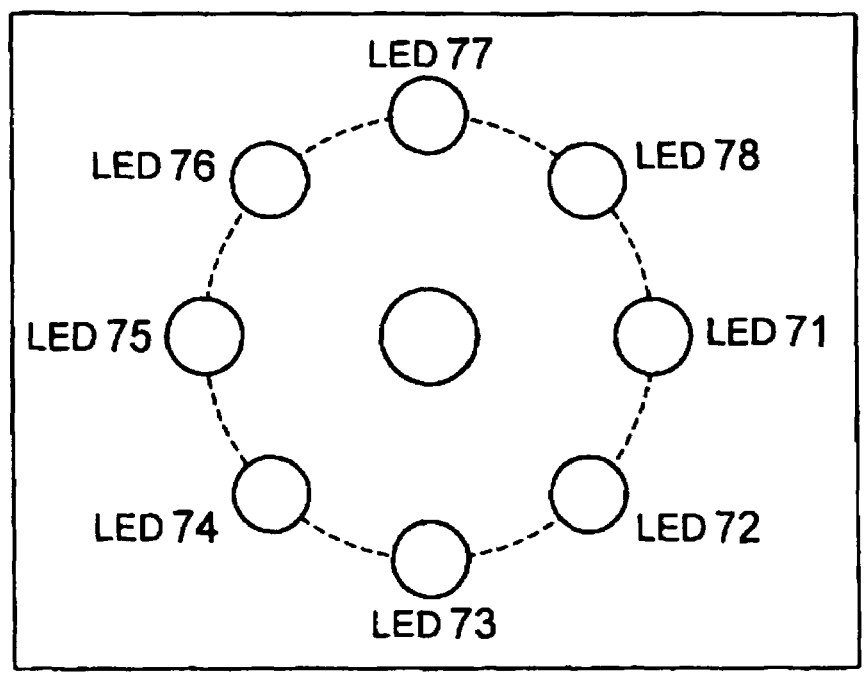
FIG. 6 is a top cross-sectional view of the arrangement of a third embodiment of the device of the invention for measuring the reflection factor.

A third embodiment of the invention is described below using FIG. 6. FIG. 6 shows this embodiment in accordance with the invention in a top view. In the figure, universal LEDs (light sources) 71 to 78 emit light with different wavelengths and are located on the circumference of a circle. The remainder of the arrangement corresponds to the elements with the same reference numbers in arrangement of FIG. 5.

This device for measuring the reflection factor with respect to a microchip (not shown) with several reaction substrates as the areas to be measured has a detector 9 which is common to several light emitting parts which each consist of a universal LED (of a light source) 71 to 78 and an aperture (not shown). The respective light emitting part (universal LED (light source) 71 to 78+ aperture) is placed directly above the respective reaction substrate. The detector 9 receives the light from the respective reaction substrate.

By this arrangement of the device for measuring the reflection factor, in addition to the action of the device for measuring the reflection factor according to the first embodiment of the invention, by switching over the light emitting parts which are in operation (universal LED light sources) 71 to 78+ apertures) per reaction substrate an increase in the rate of measurement of a host of articles can be achieved, and only a single detector 9 is needed.

Figure 7:
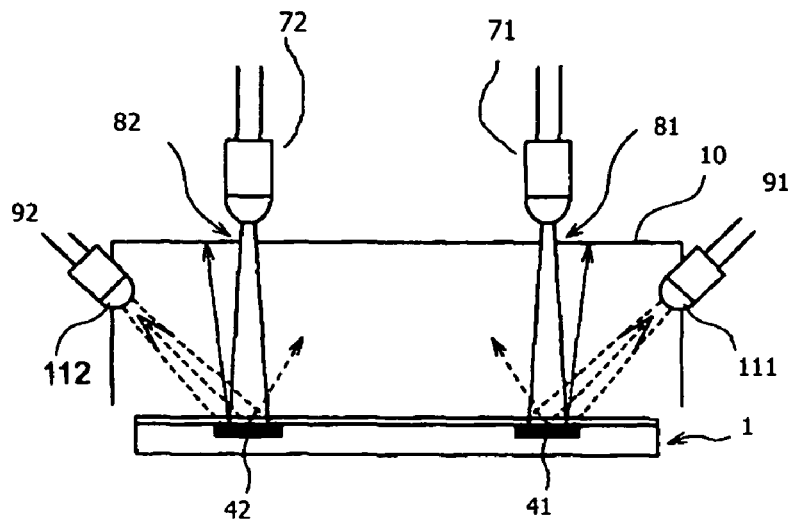
FIG. 7 is a view corresponding to that of FIG. 5, but showing a fourth embodiment of the device in accordance with the invention for measuring the reflection.

A fourth embodiment of the invention is described below using FIG. 7. Several detectors 91, 92 on their front side (light incidence side) are provided with one collecting lens 111, 112 each. The remainder of the arrangement corresponds to the elements with the same reference numbers in arrangement of FIG. 5.

This device for measuring the reflection factor with respect to a microchip 1 with several reaction substrates 41, several detectors 91, 92, and several light emitting parts which each have a universal LED (light source) 71, 72 and an aperture 81, 82. The respective light emitting part (universal LEDs (light sources) 71, 72+apertures 81, 82) is placed directly above the respective reaction substrate 41, 42. Furthermore, collecting lenses 111, 112 are located on the fronts of the light receiving parts 91, 92. The light receiving parts 91, 92 thus receive only the light from the respective corresponding reaction substrate 41, 42.

With this arrangement of the device for measuring the reflection factor, in addition to the action of the device for measuring the reflection factor according to the first embodiment, the light receiving area can be limited only to the respective reaction substrate, and thus, the effect of nonuniform reflection light (faulty radiation) from the wall of the measuring chamber 10 can be reduced. Furthermore, several articles can be measured at the same time.

What is claimed is:

1. Device for measuring the reflection factor comprising:
   at least one light emitting part from which light with a certain wavelength and directional capacity is emitted to irradiate a surface of a measurement area of a microchip which is to be measured with emitted light, and
   at least one light receiving part which receives light reflected from the measurement area for determination of the reflection factor of the measurement area,
   wherein a transparent component is located on the measurement area of the microchip,
   wherein the light emitting part is located directly above the measurement area,
   wherein the surface irradiated by the light emitting part lies within the measurement area, and
   wherein the light receiving part is located in an angular region $\theta$ (in °) which is located between angles $\theta_{min}$ and $\theta_{max}$, $\theta_{min}$ and $\theta_{max}$ (in °) being angles which the reflection light forms with respect to a normal on the edge of the irradiated surface of the area to be measured in a virtual plane which contains the emission center of the light emitting part and which is perpendicular to the microchip, wherein $\theta_{min}$ is ½ $\alpha$ and $\theta_{max}$ corresponds to $\sin^{-1}(1/n)$, where $\alpha$ (°) is the scattering angle of the light radiated by the light emitting part which is located directly above the area to be measured, and wherein n is the index of refraction of the transparent component, and in which the relationship (½)$\alpha \leq \theta \leq \sin^{-1}(1/n)$ is satisfied.

2. Device for measuring the reflection factor as claimed in claim 1, wherein in the microchip there are several areas to be measured and there is a light emitting part per measurement area, which part is located directly above the respective measurement area, and there is one light receiving part which receives light reflected from all of measurement areas and which selectively receives light from one of the measurement areas at a time.

3. Device for measuring the reflection factor as claimed in claim 1, wherein in the microchip there are several measurement areas and there is a light emitting part per measurement area, which part is located directly above the respective measurement area, and a respective light receiving part for receiving light reflected from a respective one of the measurement areas.

4. Device for measuring the reflection factor as claimed in claim 3, wherein there is a focusing lens on a light incidence side of each of the light receiving parts.

* * * * *